United States Patent
Elkind et al.

(10) Patent No.: US 6,798,521 B2
(45) Date of Patent: Sep. 28, 2004

(54) ROBUST INTEGRATED SURFACE PLASMON RESONANCE SENSOR

(75) Inventors: Jerome L. Elkind, Richardson, TX (US); Keren Deng, Plano, TX (US)

(73) Assignee: Texas Instruments Incorporated, Dallas, TX (US)

(*) Notice: Subject to any disclaimer, the term of this patent is extended or adjusted under 35 U.S.C. 154(b) by 196 days.

(21) Appl. No.: 10/053,454

(22) Filed: Oct. 25, 2001

(65) Prior Publication Data

US 2002/0085204 A1 Jul. 4, 2002

Related U.S. Application Data

(60) Provisional application No. 60/258,978, filed on Dec. 29, 2000.

(51) Int. Cl.[7] .............................................. G01N 21/55
(52) U.S. Cl. ........................................................ 356/445
(58) Field of Search ................................ 356/445, 369, 356/318, 446, 317, 43; 250/216, 225, 239

(56) References Cited

U.S. PATENT DOCUMENTS

| | | | |
|---|---|---|---|
| 5,327,225 A | * | 7/1994 | Bender et al. ............... 356/445 |
| 5,415,842 A | * | 5/1995 | Maule ...................... 422/82.05 |
| 5,770,462 A | * | 6/1998 | Molloy ....................... 436/527 |
| 5,898,503 A | | 4/1999 | Keller et al. |
| 5,912,456 A | * | 6/1999 | Melendez et al. ........... 250/216 |
| 5,946,083 A | | 8/1999 | Melendez et al. |
| 6,045,756 A | | 4/2000 | Carr et al. |
| 6,111,248 A | | 8/2000 | Melendez et al. |
| 6,111,652 A | | 8/2000 | Melendez et al. |
| 6,194,223 B1 | * | 2/2001 | Herrmann et al. ........... 436/518 |
| 6,329,209 B1 | * | 12/2001 | Wagner et al. .............. 436/518 |
| 6,529,277 B1 | * | 3/2003 | Weitekamp ................. 356/445 |

* cited by examiner

Primary Examiner—Rodney Fuller
Assistant Examiner—Andrew Sever
(74) Attorney, Agent, or Firm—Rose Alyssa Keagy; W. James Brady, III; Frederick J. Telecky, Jr.

(57) ABSTRACT

A surface plasmon resonance (SPR) sensor (10) is disclosed. The sensor (10) includes a light source (18) and polarizer (20), which emit polarized light toward a surface plasmon layer (22). Light is reflected from the surface plasmon layer (22) at many angles, toward a photodetector array (26) via a mirror surface (24). The surface plasmon layer (22) includes a resonance film (30), such as gold, and a hard protective layer (32). The hard protective layer (32) is of a thickness below the sensing range (R) of the SPR sensor (10), and protects the resonance film (30) from damage. Materials useful as the hard protective layer (32) include silicon carbide (SiC), diamond-like carbon (DLC), silicon dioxide, silicon nitride, titanium oxide, titanium nitride, aluminum oxide, aluminum nitride, beryllium oxide, and tantalum oxide.

17 Claims, 2 Drawing Sheets

ROBUST INTEGRATED SURFACE PLASMON RESONANCE SENSOR

CROSS REFERENCE TO RELATED APPLICATIONS

This application claims priority under 35 USC § 119(e)(1) of provisional application No. 60/258,978 filed Dec. 29, 2000.

STATEMENT REGARDING FEDERALLY SPONSORED RESEARCH OR DEVELOPMENT

Not applicable.

BACKGROUND OF THE INVENTION

This invention is in the field of surface plasmon resonance sensors.

Surface plasmon resonance (SPR) sensors are known for use in detecting properties of materials. In conventional SPR sensors, light at a selected wavelength is directed through a high refractive index medium to a sample under analysis, which is expected to have a lower refractive index. A resonance film, typically a very thin gold film is disposed between the two media. This film typically reflects the incident light, but electrons of some of the atoms at the medium interface resonate between conduction bands (surface plasmon resonance). In addition, because the resonance film is extremely thin, (e.g., on the order of 500 Å), an electromagnetic field component of the incident light penetrates a very short distance into the surface of the lower refractive index material (the sample medium), even when the light is substantially reflected from the film. This penetration is in the form of an exponentially attenuating evanescent wave. For incident light that is monochromatic and polarized, there is a specific angle of incidence at which the light is absorbed rather than reflected, due to resonance energy transfer between the evanescent wave and the surface plasmons. This angle, at which the reflected light intensity is at a minimum, is influenced by the properties of the material adjacent to the thin gold film. In conventional SPR sensing, a photodiode array detects the intensity of light reflected from the gold film and sample medium over a range of angles. The array is thus able to generate a signal indicating which photodiode is receiving the minimum intensity light, and thus indicating the angle of maximum absorption by the medium.

U.S. Pat. Nos. 6,045,756, 5,898,503, 5,912,456, and 5,946,083 commonly assigned herewith and incorporated by reference into this specification, describe various integrated SPR sensors. These disclosed sensors are integrated, in that the light source, light detector, high refractive index material, and gold film are all encapsulated into a single small package. The miniaturized package provided by such integration is thus well-suited for many applications, including in-line process control sensing. In addition, the integration of the SPR sensors into a monolithic device results in an optically robust device, as the optical path within the sensor remains fixed and constant. Furthermore, this integration of the sensor reduces the cost of manufacture of the sensor, and thus further facilitating widespread use of the technology. In use, the incident angle at which polarized light is absorbed by the sample medium applied to an SPR sensor is a measure of the refractive index of the sample medium. As known in the art, the refractive index of a material is determined by the composition of the material. Accordingly, measurement of the refractive index is now used to determine the purity of a supposedly pure compound, and to determine the composition of a simple mixture, such as a solution of sugar and water.

As such, SPR sensing has applicability in many manufacturing and analysis applications, including chemical processing and analysis, process control, pollution detection, and the like. For example, an important measure in the beverage industry is the sugar concentration in the beverages being produced. This measurement is not only necessary for sweet beverages, such as sweetened carbonated beverages and naturally sweet juices and drinks, but is also necessary for other less-sweet beverage, particularly alcoholic beverages such as beers and wines. SPR sensing of the sugar concentration is therefore an attractive technology in the manufacture and processing beverages.

SPR sensors are now conventionally used in spot, or sample, measurements, as well as for in-line real-time process control. For spot measurements, SPR sensors are used in handheld and tabletop instruments, where the sample to be measured is applied over a window in the instrument at which the resonance film resides; a visual display of the result of the SPR sensing is then provided by the instrument. In-line measurements are made by deploying the SPR sensor into a pipe or nozzle through which the liquid being measured passes.

It has been observed in connection with the present invention, however, that conventional SPR sensors are not sufficiently robust to provide a reasonable reliable operating life. In the case of hand-held instruments, the sample window must be wiped clean after measurement, in preparation for the next sample. However, the thin gold resonance film of conventional SPR sensors cannot withstand this wiping, and therefore conventional SPR sensors are not suitable for use for this operation. In the case of in-pipeline real-time monitoring, abrasive liquids such as tomato paste damage the thin and fragile resonance film over time. Conventional SPR sensors are therefore not useful in many of these applications, as well.

BRIEF SUMMARY OF THE INVENTION

It is therefore an object of the present invention to provide a robust surface plasmon resonance sensor that has a surface plasmon layer that can withstand repeated wiping and cleaning.

It is a further object of the present invention to provide such a sensor that can be readily integrated and miniaturized so as to be useful in process pipe applications, and sufficiently robust to be used to monitor flowing abrasive liquids.

It is a further object of the present invention to provide such a sensor that can be easily manufactured and deployed.

Other objects and advantages of the present invention will be apparent to those of ordinary skill in the art having reference to the following specification together with its drawings.

The present invention may be implemented by applying a hard thin film on the exposed surface of the surface plasmon film. This hard film must be sufficiently hard and robust so that an extremely thin layer of the hard film can adequately protect the surface plasmon film, while still permitting a reasonable thickness of the sample surface to be within the range of the evanescent resonance wave.

DETAILED DESCRIPTION OF THE INVENTION

The present invention will now be described in detail relative to a preferred embodiment, specifically in connection with an integrated surface plasmon resonance (SPR) sensor. It will be appreciated by those skilled in the art having reference to this specification that the present invention may be utilized in connection with other sensors and instruments, such alternative deployments also taking advantage of the benefits of the present invention. It is therefore contemplated that those, and other, alternative implementations of the present invention are within the scope of the invention as claimed.

Figure 1A:
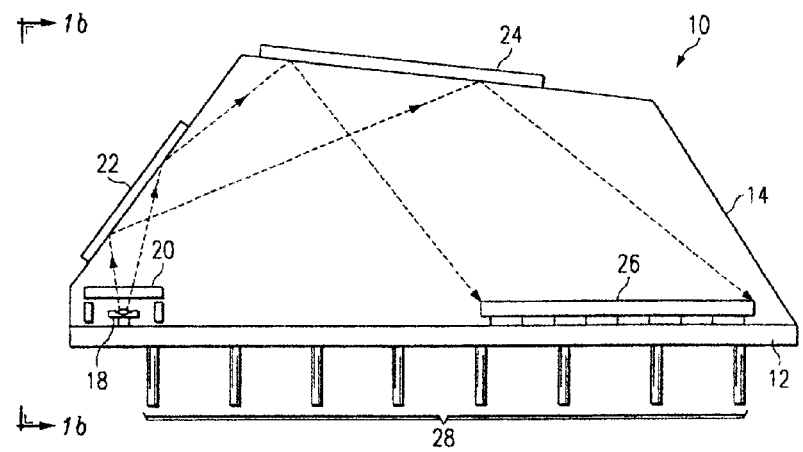
FIGS. 1a, 1b, and 1c are cross-sectional, plan, and perspective views of an integrated surface plasmon resonance (SPR) sensor according to the preferred embodiment of the invention.
Figure 1B:
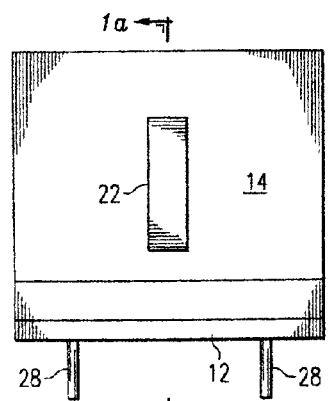
Figure 1C:
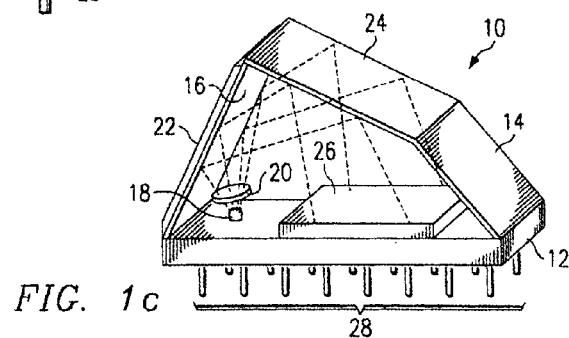

Referring now to FIGS 1a through 1c in combination, integrated SPR sensor 10 according to the preferred embodiment of the invention will now be described in detail. Much of the construction of integrated SPR sensor 10 follows that described in U.S. Pat. No. 6,111,652, commonly assigned herewith and incorporated herein by reference.

SPR sensor 10 according to this preferred embodiment of the invention is fabricated on substrate 12, which serves as a device platform by way of which the various internal components of sensor 10 may be physically mounted and electrically connected. Substrate 12 may be formed of a conventional ceramic or plastic header material, with leads 28 attached to and extending from the bottom (or sides) of substrate 12.

Light source 18 is mounted to substrate 12, and is the source of light of the desired wavelength to be used for SPR sensing. It is contemplated that a conventional light-emitting diode (LED) may be used as light source 18. Polarizer 20 is disposed over light source 18, supported from substrate 12, to polarize the light emitted by light source 18. Also mounted to substrate 12 is photodetector array 26, which is constructed of an array of photodiodes, a charge-coupled device (CCD), or other photosensitive elements, arranged into a linear (n×1) or rectangular (n×m) array. The size and geometry of photodetector array 26 will depend upon the particular arrangement of the reflective elements of SPR sensor 10, as will become apparent from the following description. The particular class of photosensor used in photodetector array 26 will generally depend upon the wavelength of light emitted by light source 18. It is desirable, for precision measurement, that the photodetectors in photodetector array 26 be as small as possible.

Light transmissive housing 14 is disposed over light source 18, polarizer 20, and photodetector array 26. Preferably, housing 14 is formed of a transparent material, such as example polycarbonate, poly(methyl methacrylate), or transparent epoxy, such as Dexter 1102. In each case, the transparent material is molded or potted over the components of SPR sensor 10. For SPR sensing, the refractive index of light transmissive housing 14 is preferably higher than that of the sample liquid or material to be sensed by SPR sensor 10.

Two reflective surfaces are provided within SPR sensor 10, to direct light emitted by light source 18 to photodetector array 26. In this embodiment of the invention, surface plasmon layer 22 is provided at a front side of SPR sensor 10, and mirror surface 24 is provided at the top of SPR sensor 10. Each of surface plasmon layer 22 and mirror surface 24 are mounted directly to light transmissive housing 14, for example by way of a thin epoxy or other adhesive. A case (not shown) may extend over the surface of light transmissive housing 14; if present, this case will have a window on the front side to expose surface plasmon layer 22 to the medium under analysis. As shown in the front plan view of FIG. 1b, surface plasmon layer 22 preferably has a longitudinal shape, extending substantially vertically along the front face of housing 14. The medium to be analyzed or sensed by SPR sensor 10 lies outside of housing 14 and in contact with surface plasmon layer 22.

As shown in FIGS. 1a and 1c, light emitted by light source 18 is polarized by polarizer 20, and is incident upon surface plasmon layer 22. This incident light reflects from surface plasmon layer 22, and is directed to mirror surface 24. Mirror surface 24, which may be any metallic or other reflective surface, in turn reflects the light to photodetector array 26. Of course, mirror surface 24 in this example is necessary because of the miniaturizing size of SPR sensor 10; alternatively, it is contemplated that the light path from light source 18 to photodetector array 26 may be arranged, by the shape of housing 14, to not require an intermediate mirror such as mirror surface 24. Further in the alternative, an intermediate mirror may be placed in the light path between light source 18 and photodetector array 26, as shown in U.S. Pat. Nos. 5,898,503 and 5,912,456, both commonly assigned herewith and incorporated herein by this reference.

Photodetector array 26 produces electrical signals corresponding to the light intensity received by each of its photodetectors, and presents these signals at leads 28. As evident from FIGS. 1a and 1c, because of the shape and construction of housing 14, the longitudinal shape and the placement of surface plasmon layer 22, and the placement of mirror surface 24, photodetector array 26 according to this preferred embodiment of the invention receives light reflected from surface plasmon layer 22 over a wide range of angles. This angular range is useful in SPR sensing, which detects variations in the reflection and absorption angles of light at surface plasmon layer 22, which correlate with the physical properties of the material under analysis that is adjacent to surface plasmon layer 22.

Figure 2:
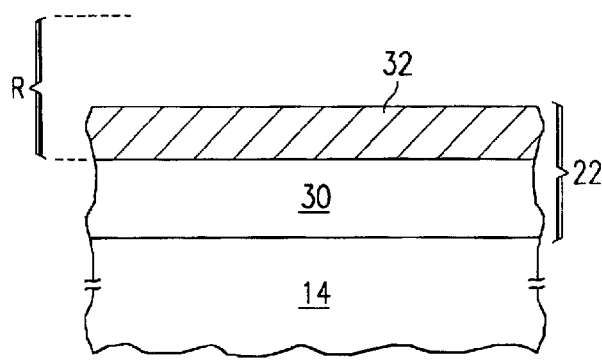
FIG. 2 is a cross-sectional diagram of a protected surface plasmon layer in the SPR sensor of FIGS. 1a and 1b according to the preferred embodiment of the invention.

Referring now to FIG. 2, surface plasmon layer 22 according to the preferred embodiment of the invention will now be described in detail. Surface plasmon layer 22 includes thin resonance film 30, with an overlying hard protective film 32. Thin resonance film 30 according to this preferred embodiment of the invention has the property that it may be placed into a state of surface plasmon resonance, upon receiving polarized incident light of a selected wavelength. As described above, in operation, this resonance occurs when incident light is substantially reflected from surface plasmon layer 22; the electromagnetic wave component of this reflected light places electrons of atoms on the far side of thin resonance film 30 into resonance between their outer conduction bands. Typically, resonance film 30 is a metal film, for which a preferred material is gold, at a thickness preferably on the order of 500 Å.

According to the preferred embodiment of the invention, surface plasmon layer 22 also includes hard protective film 32, overlying resonance film 30, so that resonance film 30 is disposed between hard protective film 32 and light transmissive housing 14. Hard protective film 32 thus protects thin resonance film 30 from mechanical damage. For example, in situations where SPR sensor 10 is used to measure the properties of samples, and where wiping of the surface of surface plasmon layer 22 is required between samples, hard protective film 32 protects fragile resonance film 30 from scratching and other damage due to such wiping and cleaning. In addition, SPR sensor 10 according to this embodiment of the invention may be used in real-time analysis of liquids even if the medium under analysis includes abrasive elements, such as in the case of tomato paste.

Hard protective film 32 preferably meets various constraints in its application to SPR sensor 10, according to the preferred embodiment of the invention. Hard protective film 32 should be capable of providing adequate mechanical protection at thicknesses that are below the SPR sensing range. As known in the art, SPR sensing is a surface technique, in that the evanescent wave produced by the resonance state has a usable amplitude that extends only a short distance, for example 2000 Å, from the outer surface of resonance film 30. Accordingly, hard protective film 32 must be capable of providing the desired protection, without consuming the SPR sensing range. This relationship is illustrated in FIG. 2, where range R corresponds to the SPR sensing range, extending in this example beyond the thickness of hard protective film 32 and thus into the medium under analysis. For example, for an SPR sensing range of about 1000 Å, hard protective film 32 is preferably on the order of 350 Å. Additionally, hard protective film 32 should be sufficiently hard so as to be cleanable between the measurement of samples, and upon removal of SPR sensor 10 from the medium, for example for periodic maintenance. Further, hard protective film 32 should be readily depositable over resonance film 30, according to proven techniques such as chemical vapor deposition (CVD), plasma enhanced CVD (PECVD), and evaporation, among others.

According to the preferred embodiment of the invention, a number of materials are contemplated to meet these constraints. Preferred examples of such materials are silicon carbide (SiC), and diamond-like carbon (DLC). Other examples of materials suitable for use as hard protective film 32 include silicon dioxide, silicon nitride, titanium oxide, titanium nitride, aluminum oxide, aluminum nitride, beryllium oxide, and tantalum oxide. These materials can all be deposited by way of CVD or PECVD, and thus are especially suitable for use in integrated SPR sensor 10 according to the preferred embodiment of the invention. It is also contemplated that other materials besides those listed above may also be suitable for use as hard protective film 32.

In operation, SPR sensor 10 is exposed to the medium to be analyzed, by placing this medium adjacent to hard protective film 32 at the surface of surface plasmon layer 22. Light emitted by light source 18, and polarized by polarizer 20, impinges upon resonance film 30 of surface plasmon layer 22. This light is reflected from resonance film 30 to mirror surface 24, and is reflected from mirror surface 24 to photodetector array 26. As evident from FIGS. 1a and 1c, the multiple light paths correspond to many different angles of incidence on resonance film 30, with each position in photodetector array 26 corresponding to a corresponding angle of incidence.

Because of the surface plasmon resonance effect, light will be absorbed by the medium at a particular angle of incidence. This angle depends upon certain properties of the material, such as the mass concentration of biochemically relevant molecules, e.g., sugars. Light from other angles of incidence will be substantially fully reflected. As such, there will be a location of photodetector array 26 at which the reflected light intensity will be at a minimum; the photodetector at this location will produce a signal indicative of a low intensity of received light, while other photodetectors will be producing signals indicating higher intensity. Interrogation of the photodetectors, in combination with knowledge of the geometry of SPR sensor 10, will thus provide an indication of the angle of absorption of the material. Through conventional calibration and monitoring methods, the medium can be analyzed relative to the relevant parameter.

SPR sensor 10 according to this preferred embodiment of the invention thus provides a robust sensor for use in the monitoring and analysis of many harsh and hostile liquids, including those found in the beverage industry that can abrade the critical surface of its surface plasmon layer 22. The protective capability provided by hard protective film 32 permits deployment of SPR sensor 10 as a monitoring device in a liquid pipe, and in a handheld or table-top instrument.

Figure 3:
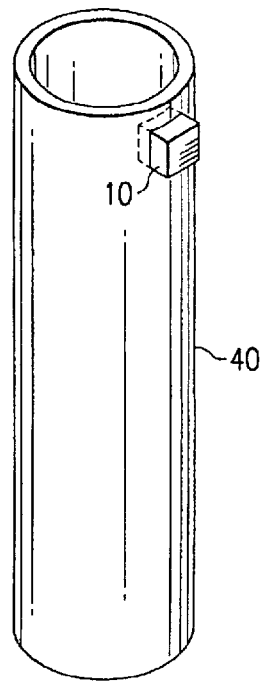
FIG. 3 is a plan view illustrating the deployment of the SPR sensor of FIGS. 1a and 1b according to the preferred embodiment of the invention in a beverage pipeline application.

As shown in FIG. 3, SPR sensor 10 is attached to pipe 40, through an orifice (not shown). In this arrangement, surface plasmon layer 22 of SPR sensor 10 extends into the interior of pipe 40; leads 28 extend externally from pipe 40 to provide connection to the appropriate monitoring system. According to this deployment, liquid flowing through pipe 40 will contact surface plasmon layer 22 of SPR sensor 10, and will exhibit angles of absorption to SPR sensor 10 that will be communicated by SPR sensor 10 to the monitoring system. Because of the robustness of SPR sensor 10 provided by hard protective film 32, this use of SPR sensor 10 in connection with abrasive liquids is enabled. The benefits of small integrated SPR sensor 10 can thus be obtained in these applications as well, such benefits being substantial when compared against the cumbersome and costly critical angle refractometers that are now conventionally used in these situations. Additionally, it is contemplated that SPR sensor 10 will have longer field life, given the robustness provided by hard protective film 32.

Figure 4:
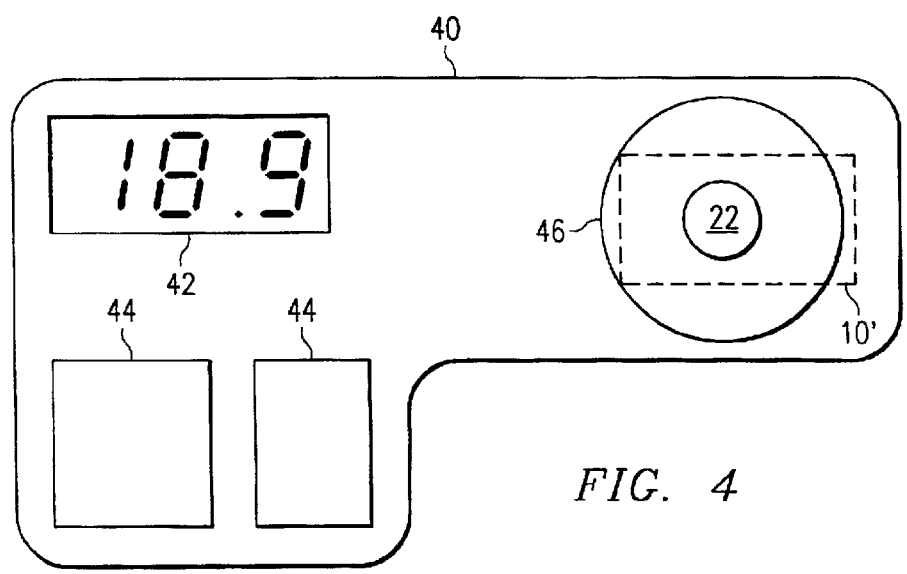
FIG. 4 is a plan view illustrating a handheld instrument including the SPR sensor of FIGS. 1a and 1b according to the preferred embodiment of the invention.

FIG. 4 illustrates the deployment of SPR sensor 10' according to the preferred embodiment of the invention, in handheld instrument 40. A desktop instrument may be similarly configured, but will of course have a larger size and different shape. As shown in FIG. 4, SPR sensor 10' is deployed within the housing of instrument 40, with surface plasmon layer 22, having hard protective film 32 overlying resonance film 30 as described above, exposed at an opening within sample funnel 46. SPR sensor 10' is constructed as described above, but may have a modified shape that fits the desired form factor of instrument 40. Electronic circuitry (not shown) is included within instrument 40, for controlling the operation of instrument 40, including receiving and processing signals output by photodetector array 26 in SPR sensor 10'. The result of SPR sensing of a liquid sample dropped into funnel 46 onto surface plasmon layer 22 is indicated by visual display 42, with the operation of instrument 40 controlled by the user via buttons 44.

Following the measurement of the refractive index of a sample dropped onto surface plasmon layer 22, the user will clean surface plasmon layer 22, typically by rinsing the surface and wiping it with an absorbent cloth, to ensure that the next sample is not contaminated with the prior sample. Because of hard protective film 32, resonance film 30 in sensor 10' is not damaged by this cleaning and wiping. According to the present invention, SPR sensor 10' thus remains robust over many uses.

While the present invention has been described according to its preferred embodiments, it is of course contemplated that modifications of, and alternatives to, these embodiments, such modifications and alternatives obtaining the advantages and benefits of this invention, will be apparent to those of ordinary skill in the art having reference to this specification and its drawings. It is contemplated that such modifications and alternatives are within the scope of this invention as subsequently claimed herein.

We claim:

1. A surface plasmon resonance sensor, comprising:
   a source of polarized light at a selected wavelength;
   a surface plasmon layer, comprising:
      a resonance film, formed of a selected material to a selected thickness so that the polarized light from the source establishes surface plasmon resonance at a surface of the resonance film, the surface plasmon resonance producing an evanescent wave extending away from the surface of the resonance film over a sensing range; and
      a hard protective film that is not an attachment layer and overlies the surface of the resonance film, the hard protective film having a thickness that is substantially less than the sensing range;
   a light transmissive medium disposed between the source and the surface plasmon layer; and
   a photodetector array, for detecting intensity of polarized light reflected from the resonance film.

2. The sensor of claim 1, wherein the hard protective film consists essentially of a material selected from the group consisting of silicon carbide, diamond-like carbon, titanium nitride, and aluminum nitride.

3. The sensor of claim 1, wherein the resonance film comprises gold.

4. The sensor of claim 1, further comprising:
   an intermediate mirror, positioned relative to the photodetector array so as to reflect, to the photodetector array, polarized light reflected from the resonance film.

5. The sensor of claim 4, wherein the light transmissive medium is a housing disposed over the source and the photodetector array;
   and wherein the surface plasmon layer and the intermediate mirror are mounted to surfaces of the housing.

6. The sensor of claim 1, wherein the light transmissive medium is a housing disposed over the source and the photodetector array;
   and wherein the surface plasmon layer and the intermediate mirror are mounted to surfaces of the housing.

7. The sensor of claim 1, wherein the source comprises:
   a light-emitting diode; and
   a polarizing element disposed between the light-emitting diode and the surface plasmon layer.

8. The sensor of claim 1, further comprising:
   a substrate, to which the source and photodetector array are physically mounted; and
   a plurality of leads, electrically connected to the photodetector array.

9. A surface plasmon resonance sensor, comprising:
   a source of polarized light at a selected wavelength;
   a surface plasmon layer, comprising:
      a resonance film; and
      an overlying hard protective film, consisting essentially of a material selected from the group consisting of silicon carbide, and diamond-like carbon;
   a light transmissive medium disposed between the source and the surface plasmon layer; and
   a photodetector array, for detecting intensity of polarized light reflected from the resonance film.

10. The sensor of claim 9, wherein the resonance film comprises gold.

11. The sensor of claim 9, further comprising:
    an intermediate mirror, positioned relative to the photodetector array so as to reflect, to the photodetector array, polarized light reflected from the resonance film.

12. The sensor of claim 11, wherein the light transmissive medium is a housing disposed over the source and the photodetector array;
    and wherein the surface plasmon layer and the intermediate mirror are mounted to surfaces of the housing.

13. The sensor of claim 9, wherein the light transmissive medium is a housing disposed over the source and the photodetector array;
    and wherein the surface plasmon layer and the intermediate mirror are mounted to surfaces of the housing.

14. The sensor of claim 9, wherein the source comprises:
    a light-emitting diode; and
    a polarizing element disposed between the light-emitting diode and the surface plasmon layer.

15. The sensor of claim 9, further comprising:
    a substrate, to which the source and photodetector array are physically mounted; and
    a plurality of leads, electrically connected to the photodetector array.

16. An instrument for measuring the refractive index of a liquid, comprising:
    a housing, having an opening;
    a surface plasmon sensor, comprising:
       a source of polarized light at a selected wavelength;
       a surface plasmon layer exposed through the opening in the housing, and comprising:
          a resonance film, formed of a selected material to a selected thickness so that the polarized light from the source establishes surface plasmon resonance at a surface of the resonance film, the surface plasmon resonance producing an evanescent wave extending away from the surface of the resonance film over a sensing range; and
          a hard protective film that is not an attachment layer and overlies the surface of the resonance film, the hard protective film having a thickness that is substantially less than the sensing range;
       a light transmissive medium disposed between the source and the surface plasmon layer; and
       a photodetector array, for detecting intensity of polarized light reflected from the resonance film; and
    an output device for outputting an indication based upon an angle at which the polarized light is absorbed by a sample medium dispensed into the opening.

17. The instrument of claim 16, wherein the hard protective film consists essentially of a material selected from the group consisting of silicon carbide, diamond-like carbon, titanium nitride, and aluminum nitride.

* * * * *